(12) United States Patent
Ando

(10) Patent No.: US 9,943,213 B2
(45) Date of Patent: Apr. 17, 2018

(54) MEDICAL IMAGE PROCESSING APPARATUS GENERATING A THREE-DIMENSIONAL IMAGE OF A MEDICAL DEVICE SUPERPOSED OVER A THREE-DIMENSIONAL IMAGE OF A PREOPERATIVE STRUCTURE OF AN OBJECT

(71) Applicant: CANON KABUSHIKI KAISHA, Tokyo (JP)

(72) Inventor: Hirotake Ando, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 963 days.

(21) Appl. No.: 13/910,947

(22) Filed: Jun. 5, 2013

(65) Prior Publication Data

US 2013/0329024 A1    Dec. 12, 2013

(30) Foreign Application Priority Data

Jun. 8, 2012 (JP) ................................. 2012-131118

(51) Int. Cl.
 *A61B 1/04* (2006.01)
 *A61B 1/00* (2006.01)
 *A61B 90/00* (2016.01)

(52) U.S. Cl.
 CPC ........ *A61B 1/00009* (2013.01); *A61B 1/0005* (2013.01); *A61B 90/37* (2016.02); *A61B 2090/364* (2016.02)

(58) Field of Classification Search
 CPC ... A61B 1/00009; A61B 1/0005; A61B 90/37; A61B 1/00006; A61B 5/065; A61B 5/066; A61B 8/4254; A61B 2090/364–2090/367; A61B 1/00; A61B 1/04; H04N 13/0239; H04N 2005/2255; H04N 5/2254; H04N 5/2259; H04N 13/004; H04N 13/0048; H04N 13/0055; H04N 13/0275; H04N 13/0285; H04N 13/0296; H04N 13/0438; H04N 13/0497; H04N 5/2251; H04N 5/02
 USPC ............................................................ 348/65
 See application file for complete search history.

(56) References Cited

U.S. PATENT DOCUMENTS

| 6,473,635 B1 * | 10/2002 | Rasche | ..................... | A61B 5/06 600/424 |
| 6,522,908 B1 * | 2/2003 | Miyashita | ............ | A61B 5/0064 600/409 |
| 8,353,818 B1 * | 1/2013 | Sasaki | ..................... | A61B 5/061 396/17 |

(Continued)

FOREIGN PATENT DOCUMENTS

| JP | S64-62115 A | 3/1989 |
| JP | 05177000 A | 7/1993 |
| JP | 2000-279376 A | 10/2000 |

(Continued)

*Primary Examiner* — Jessica M Prince
(74) *Attorney, Agent, or Firm* — Canon USA Inc., IP Division

(57) ABSTRACT

A medical image processing apparatus comprises an image information processor that generates image information for acquiring a superposed image having a three-dimensional image of a medical device over a three-dimensional image of a preoperative structure of an object to which the medical device is inserted, and outputs the image information of the superposed image to a display apparatus.

5 Claims, 6 Drawing Sheets

(56) References Cited

U.S. PATENT DOCUMENTS

| | | | |
|---|---|---|---|
| 2007/0053555 A1* | 3/2007 | Ooi | A61B 6/461 382/128 |
| 2008/0097159 A1* | 4/2008 | Ishiguro | A61B 1/0051 600/145 |

FOREIGN PATENT DOCUMENTS

| | | |
|---|---|---|
| JP | 2001-204738 A | 7/2001 |
| JP | 2007-209531 A | 8/2007 |
| JP | 2011-104053 A | 6/2011 |
| JP | 2011-189074 A | 9/2011 |
| JP | 2011-193885 A | 10/2011 |
| JP | 2011-212245 A | 10/2011 |
| WO | 2011/102012 A1 | 8/2011 |

\* cited by examiner

MEDICAL IMAGE PROCESSING APPARATUS GENERATING A THREE-DIMENSIONAL IMAGE OF A MEDICAL DEVICE SUPERPOSED OVER A THREE-DIMENSIONAL IMAGE OF A PREOPERATIVE STRUCTURE OF AN OBJECT

BACKGROUND OF THE INVENTION

Field of the Invention

The present invention relates to medical image processing apparatuses which accurately visualize an operating environment for a medical device, such as an endoscope, to be inserted to an object.

Description of the Related Art

It is difficult to insert a surgical tool, such as an endoscope and a catheter, having a complicated form to an intended region through an internal luminal structure such as blood vessel or a body cavity, for example.

Accordingly, Japanese Patent Laid-Open No. 5-177000 discloses creating a map of an internal luminal structure from an image of an internal luminal structure captured with an X-ray or by CT, MRI or the like before an operation and performing navigation for inserting a tip of a surgical tool into an internal desirable position.

For an intraoperative navigation, a position of a tip of a surgical tool may be detected with an X-ray. Alternatively, a transmitting unit may be attached to the tip of the surgical tool and a signal transmitted from the transmitting unit may be received by a receiving unit. The position of the transmitting means is acquired from the received signal in real time. The position may be displayed over the map.

According to the method disclosed in Japanese Patent Laid-Open No. 5-177000, a two-dimensional map is used. Therefore, what kind of attitude a surgical tool has may not be known three-dimensionally.

SUMMARY OF THE INVENTION

According to the present invention, there is provided a medical image processing apparatus including:
  an input unit used to input change-of-form information on a medical device;
  an image signal generating unit which generates an image signal from the input change-of-form information;
  an image information generating unit which generates image information for acquiring a superposed image having a three-dimensional image of the medical device over a three-dimensional image a preoperative structure; and
  an output unit which outputs information on the superposed image.

Further features of the present invention will become apparent from the following description of exemplary embodiments with reference to the attached drawings.

DESCRIPTION OF THE EMBODIMENTS

First Embodiment

Figure 1:
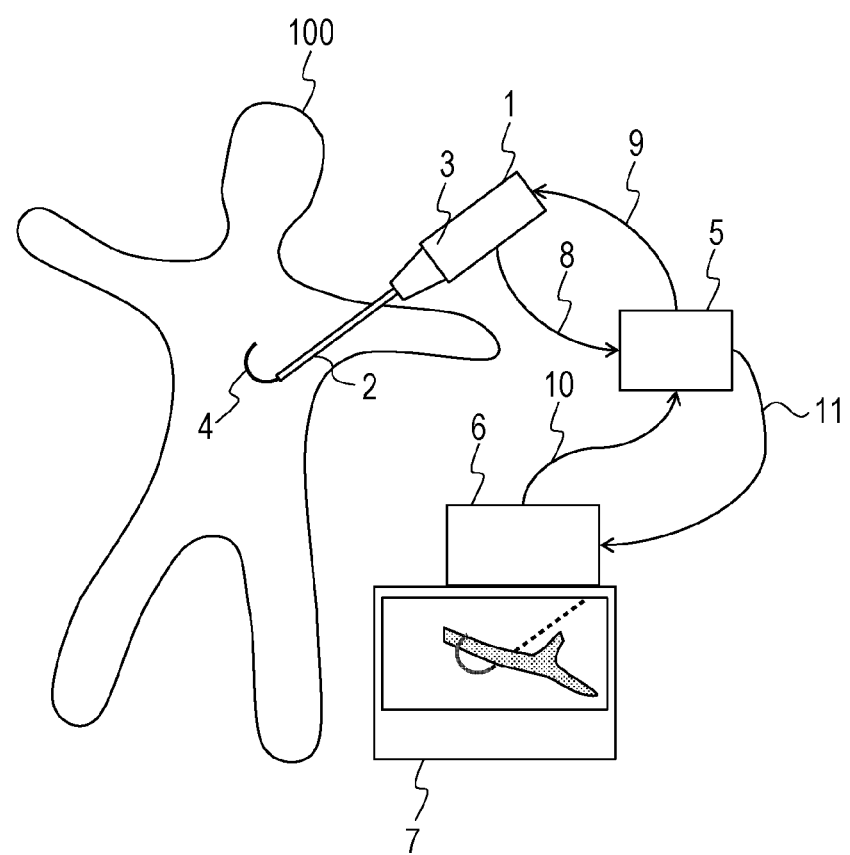
FIG. 1 is a schematic diagram illustrating a system having a medical image display apparatus according to a first embodiment.

A medical image processing apparatus according to a first embodiment of the present invention includes an image information generating unit which causes a display apparatus to display a three-dimensional image of a medical device over a three-dimensional image of a preoperative object (or an object before an operation and/or before an examination).

First, reference numerals in drawings will be described. Reference numeral 1 denotes a medical device, reference numerals 4 and 401 denote curvature deformation units, reference numeral 5 denotes a controller, reference numeral 6 denotes a navigation unit, and reference numeral 101 denotes an internal structure.

FIG. 1 is a schematic diagram of a system including a medical image processing apparatus according to the first embodiment. A medical device 1 is inserted to an object 100 which is a subject human body during an operation. The medical device 1 has an operating unit 3 and an inserting unit 2. The inserting unit 2 has a curvature deformation unit 4 at its leading end. The curvature deformation unit 4 curves (or bends) to the direction of in-plane as illustrated, for example, with an internally-contained wire. When the medical device is an endoscope, the curvature deformation unit may internally contain an image optical system such as optical fiber and/or a treatment tool.

The medical device 1 is connected to the controller 5 through cables 8 and 9. The controller 5 automatically controls operating conditions such as an insertion depth, direction and/or angle of the inserting unit 2 or a position and/or direction of rotation of the medical device 1 itself, in addition to control over a deformation of the curvature deformation unit 4. The controller 5 is connected to the navigation unit 6 that is a medical image processing apparatus according to this embodiment through cables 10 and 11. The navigation unit 6 outputs image information, and a display apparatus 7 receives it and displays the corresponding image. In FIG. 1, the display apparatus 7 three-dimensionally displays images of a blood vessel to be observed, a part of the inserting unit 2, and the curvature deformation unit 4.

Figure 2:
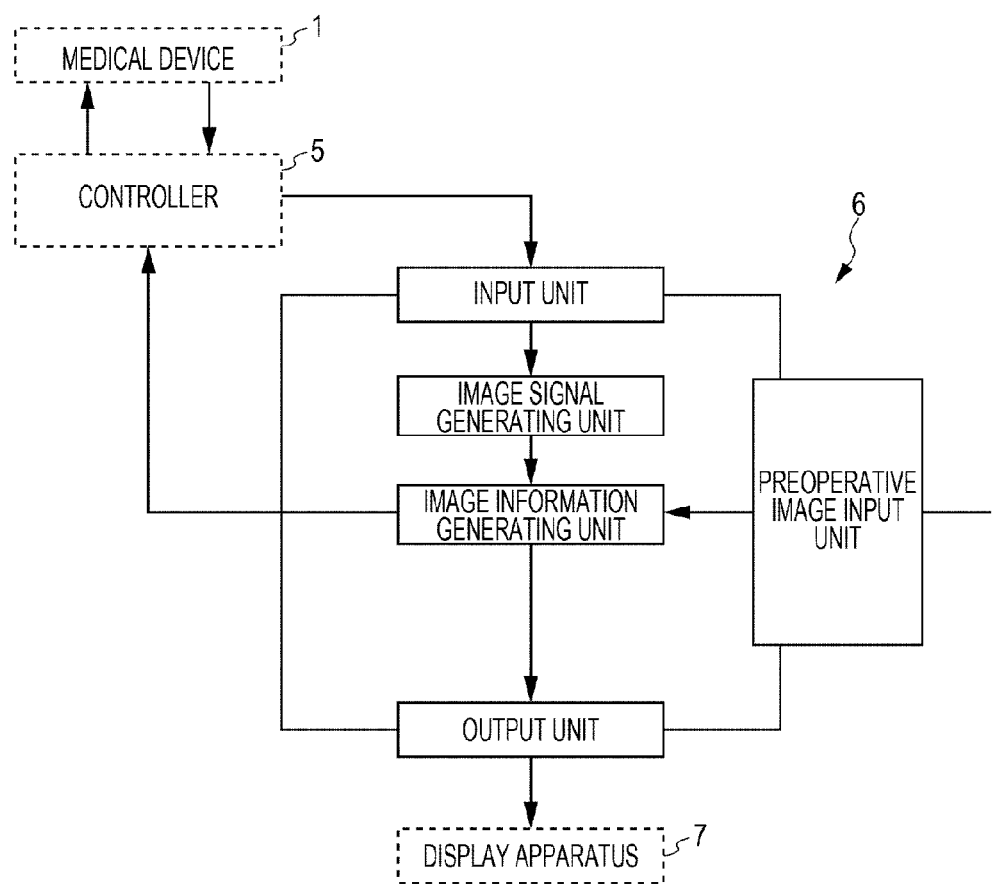
FIG. 2 is a schematic diagram illustrating a configuration of a medical image display apparatus according to the first embodiment.

FIG. 2 is a schematic diagram illustrating a configuration of the navigation unit 6 that is a medical image processing apparatus according to this embodiment. The navigation unit 6 has a preoperative image input unit, an input unit which receives information from the medical device, an image signal generating unit which generates an image signal from information from the medical device, an image information generating unit, and an output unit which outputs image information generated by the image information generating unit to a display apparatus.

The preoperative image input unit receives a plurality of two-dimensional tomograms captured before an operation. The image information generating unit segments the plurality of input tomograms to generate a three-dimensional image.

A two-dimensional image captured before an operation here may refer to an image captured by an apparatus such as a CT and an MRI, for example. The image is an image of a wider area than an area to be displayed by a display apparatus. The two-dimensional image has in advance a marker that is a coordinate reference for image capturing such that the curvature deformation unit of the medical device may be displayed at a correct position in a preoperative image.

The image signal generating unit generates an image signal on the basis of change-of-form information input from the medical device 1 to the input unit. The change-of-form information from the medical device 1 may refer to tip position information, change-of-angle information, change-of-tilt information, and/or change-of-pressure information, for example, on the curvature deformation unit 4, which may be acquired by insertion of the curvature deformation unit to an object. From at least one information piece of these information pieces input through the controller 5, the image information generating unit generates image information for generating a three-dimensional image of a form of the curvature deformation unit 4 in the medical device 1. The form of the curvature deformation unit 4 may be a thickness of the curvature deformation unit or a contour of the leading end, for example.

Another information piece for identifying a form of the curvature deformation unit may be information known before the curvature deformation unit is inserted to an object, such as a structure of the curvature deformation unit, an angle of a curvature deformation, and a range that may be captured by an imaging optical system if the curvature deformation unit has one. These known information pieces may be input from the controller 5 to the navigation unit 6 or may be directly input to the navigation unit through an input unit, not illustrated, without through the controller 5.

The image information generating unit generates image information for displaying an image (superposed image) having a three-dimensional image of the curvature deformation unit 4 over a preoperative three-dimensional image of an object. Image information on a superposed image is transmitted from the output unit to the display apparatus, and the display apparatus displays a three-dimensional image that is the superposed image.

The display apparatus may be a display for a PC, for example. The navigation unit 6 generates image information on a rotatable and translational image from a viewpoint requested by an observer.

Thus, the medical image processing apparatus according to this embodiment may three-dimensionally display a figure of the medical device over a three-dimensional image generated on the basis of a preoperative image.

The figure of the medical device to be displayed in the medical image processing apparatus according to this embodiment is a form of the curvature deformation unit of the medical device as described above. The figure of the medical device to be displayed in the medical image processing apparatus according to the present invention may include both figures of the curvature deformation unit and the inserting unit. The figure of the inserting unit may be generated from information acquired by insertion of the curvature deformation unit or known information, like a figure of the curvature deformation unit.

In a system having a medical image processing apparatus according to this embodiment, the controller 5 may automatically perform operations on a position, a depth, an angle and/or a direction, for example, of the medical device itself, the inserting unit or the curvature deformation unit. On the other hand, in a system according to the present invention, one of those operations may be performed manually by an operator.

A system having a medical image processing apparatus according to this embodiment may perform an operation on a subject human body as the object 100. On the other hand, a system having a medical image processing apparatus according to the present invention may perform an operation on an animal as its object. A system having a medical image processing apparatus according to this embodiment may perform an operation on a subject human body as the object 100, and the medical device may be inserted into the illustrated body cavity. On the other hand, a system having a medical image processing apparatus according to the present invention may be inserted to the body from the mouth, an ear or the like or may be inserted to a lumen such as a gap in the brain, a colon, or a blood vessel.

In a system having a medical image processing apparatus according to this embodiment, information pieces as described above may be moved (received and/or transmitted) through a cable or by radio between the operation controller 5 of the medical device and the navigation unit 6.

In a system having a medical image processing apparatus according to this embodiment, information may be moved through a cable or by radio between the navigation unit 6 and the display apparatus 7.

In a system having a medical image processing apparatus according to this embodiment, information pieces as described above may be moved through a cable or by radio between components of the navigation unit 6.

Figure 3A:
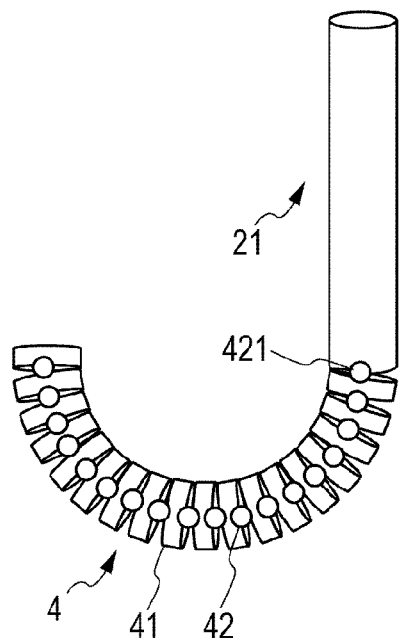
FIGS. 3A and 3B are schematic diagrams of a curvature deformation unit of a medical device of a system in the medical image display apparatus according to the first embodiment.
Figure 3B:
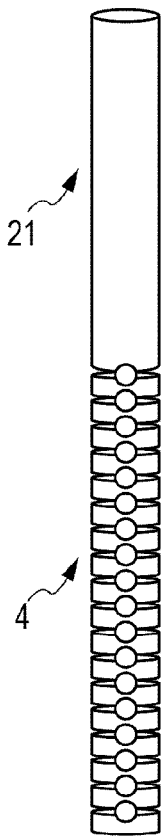

FIGS. 3A and 3B are schematic diagrams illustrating a part (rigid unit) 21 and the curvature deformation unit 4 at its tip of the inserting unit of the medical device 1 in a system having the medical image processing apparatus. FIG. 3A illustrates the curvature deformation unit 4 that is bending, and FIG. 3B illustrates the curvature deformation unit 4 that is straight and is not bending.

The curvature deformation unit 4 has a plurality of node rings 41 in a longitudinal direction. A fulcrum 42 is provided between the node rings 41. The curvature deformation unit 4 is curved (rotated) about the fulcrums.

The straight state in FIG. 3B according to this embodiment is an initial state. The controller 5 recognizes the state as the initial state and recognizes a state resulting from a curvature deformation two-dimensionally, that is, simply recognizes a form of the state.

From the state, the position where the medical device 1 is mounted (or a tilt or a distance from an object, for example) and a marker on a preoperative image, the navigation unit 6 calculates the position of the medical device on a three-dimensional image for registration, and the image information generating unit generates superposed image information.

Figure 4A:
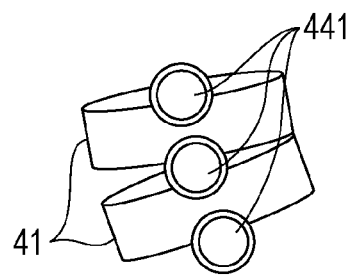
FIGS. 4A and 4B are schematic diagrams illustrating the curvature deformation unit having an angle sensor.
Figure 4B:
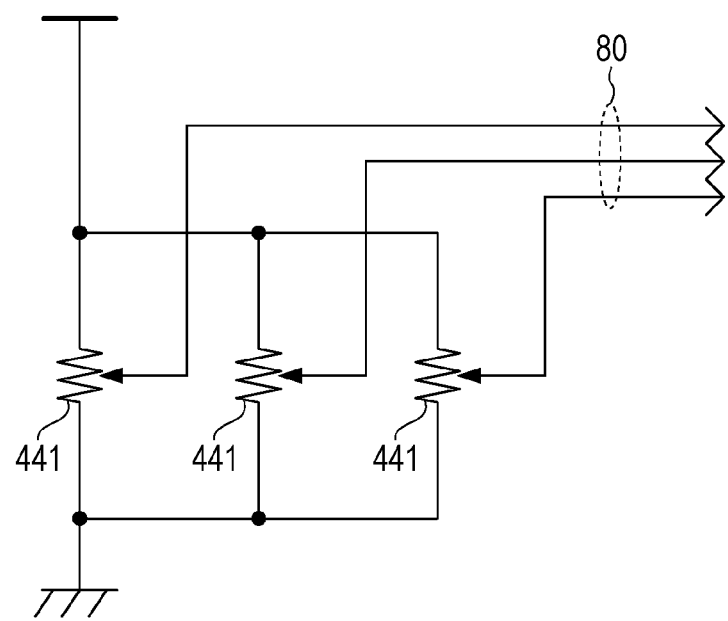
Figure 5:
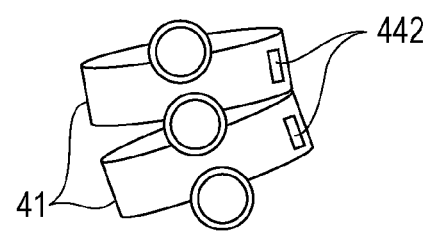
FIG. 5 is a schematic diagram illustrating the curvature deformation unit having an attitude sensor.
Figure 6:
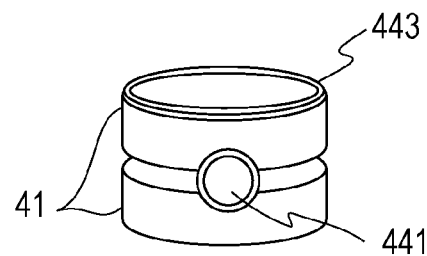
FIG. 6 is a schematic diagram illustrating the curvature deformation unit having a pressure sensor.

FIGS. 4A and 4B to FIG. 6 are schematic diagrams illustrating configurations of the various curvature deformation units 4. FIGS. 4A and 4B illustrate a configuration in which the curvature deformation unit has a potentiometer and which provides change-of-angle information. FIG. 5 illustrates a configuration in which the curvature deformation unit has an attitude sensor and which provides information on a change of direction or attitude. FIG. 6 illustrates a configuration in which the curvature deformation unit has a pressure sensor and which provides change-of-pressure information.

The configurations of the various curvature deformation units will be described with reference to FIGS. 4A and 4B to FIG. 6.

As illustrated in FIG. 4A, the curvature deformation unit has a plurality of node rings 41 and a potentiometer 441 at each fulcrum therebetween. Each of the potentiometers 411 detects an angle of the corresponding node ring as a value of resistance. FIG. 4B illustrates an equivalent circuit of three potentiometers illustrated in FIG. 4A. The three potentiometers 441 give voltages based on the corresponding angles as change-of-angle information to the controller 5.

As illustrated in FIG. 5, the curvature deformation unit has a plurality of node rings 41, and each of the node rings has an attitude sensor 442 at a same position on its side. The attitude sensor 442 may be a triaxial acceleration sensor, for example. The attitude sensor 442 may detect the direction of gravity in three directions applied to the sensor, that is, a tilt of the corresponding node ring (tilt of the attitude sensor) and give change-of-attitude information to the controller 5. Because the three-dimensional directions of the node rings 41 is provided by the attitude sensors, the controller 5 may grasp the attitude of the curvature deformation unit three-dimensionally rather than two-dimensionally. The change-of-attitude information may also be useful for generating a three-dimensional image fast and accurately by the navigation unit 6 even when the controller 5 does not grasp the attitude three-dimensionally.

Because the three-dimensional directions of the node rings 41 are provided by the attitude sensors, the attitude of the curvature deformation unit may be detected three-dimensionally even when the curvature deformation unit only moves two-dimensionally as in this embodiment. Thus, the attitude may be detected even when the curvature deformation unit 4 is compressed by an internal structure and is tilted to a direction where it is not operable.

The attitude sensor may be an encoder, an optical sensor or the like instead of an acceleration sensor.

As illustrated in FIG. 6, the curvature deformation unit has a plurality of node rings 41 and a potentiometer 441 and a pressure sensor 443 therebetween. The pressure sensor 443 outputs a voltage in accordance with a pressure. The pressure sensor may be a piezoresistive pressure sensor which is produced by an MEMS technology, for example.

The change-of-pressure information on the curvature deformation unit is given to the controller 5. On the basis of the change-of-pressure information, operation control information may be transmitted from the navigation unit 6 to the controller 5. For example, when the controller 5 inserts the curvature deformation unit automatically, the navigation unit 6 determines that the curvature deformation unit is in contact with an internal structure on the basis of the change-of-pressure information. How much the curvature deformation unit is to be retracted may be instructed through the controller 5.

Second Embodiment

A medical image processing apparatus according to a second embodiment of the present invention is a medical image processing apparatus which corrects an image of an abutted part of an image corresponding to an internal structure in a superposed image to enlarge the image of the form of the internal structure in the abutted part when the curvature deformation unit is abutted against the internal structure. Except for this, the second embodiment is the same as the first embodiment.

Figure 7A:
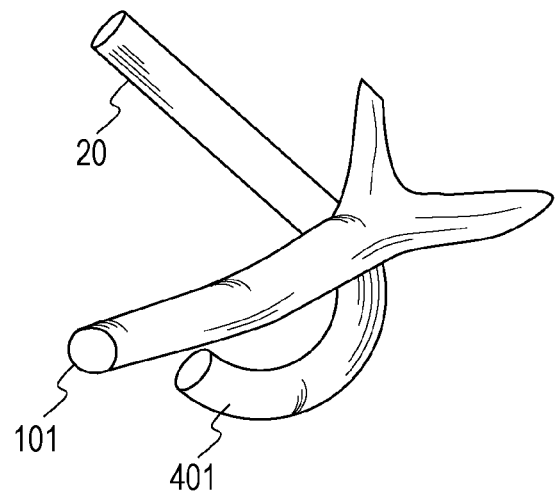
FIGS. 7A and 7B are schematic diagrams illustrating that a part abutted against the curvature deformation unit of an internal structure is corrected to be enlarged by an image correction in a superposed image.
Figure 7B:
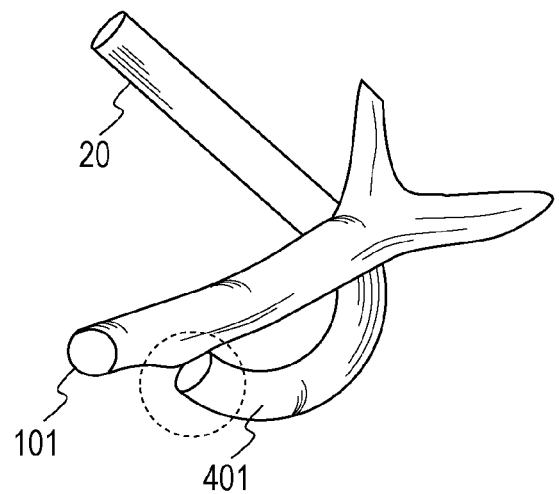

FIGS. 7A and 7B are schematic diagrams illustrating three-dimensional images based on image information output by the medical image processing apparatus according to this embodiment. FIGS. 7A and 7B illustrate superposed images in which images of an internal structure and a curvature deformation unit are superposed. Reference numeral 20 denotes an inserting unit, reference numeral 401 denotes a curvature deformation unit, and reference numeral 101 denotes an internal structure. FIG. 7A is a schematic diagram illustrating a tip of the curvature deformation unit immediately before it is abutted against an internal structure. FIG. 7B is a schematic diagram illustrating an image corrected to enlarge the image of the abutted internal structure.

The internal structure and the curvature deformation unit may be abutted against each other when insertion of the automatically controlled medical device gets slower during an operation. Thus, when the insertion condition changes, the fact is determined by the navigation unit on the basis of the change-of-form information on the medical device, and the image of the abutted internal structure (within a dotted circle) is corrected to be enlarged.

More specifically, if the tip of the curvature deformation unit having a pressure sensor in its leading part detects a pressure and it is known that an internal structure exists near there from a preoperative image or a preoperative three-dimensional image before a superposed image, the image is corrected to enlarge the image of the internal structure.

Thus, when the structure of an object to which the medical device is inserted is different from the structure grasped from a preoperative image in their sizes and/or positions, the image correction may provide a more accurate image thereof.

Having described this embodiment in which a medical device having a curvature deformation unit having a pressure sensor at its tip, a medical image processing apparatus according to the present invention may have pressure sensors at a plurality of parts such as a tube part and a stick part of the curvature deformation unit, and an image of an internal structure may be corrected to be enlarged from pressures on the tube part and/or stick part.

According to this embodiment, when the curvature deformation unit is abutted against an internal structure, an image correction is performed to enlarge the image of the contact part of the internal structure. On the other hand, a medical image processing apparatus according to the present invention may perform an image correction to delete or reduce an image of a part of an internal structure expected from a preoperative image to be abutted as a result of the insertion or deformation of the curvature deformation unit if it is not abutted against the part.

As specifically described with reference to the embodiments, a medical image processing apparatus of the present invention may provide a superposed image in which a three-dimensional image of the medical device is over a three-dimensional image of a preoperative structure. Thus, an accurate three-dimensional image based on information may be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-131118, filed Jun. 8, 2012, which is hereby incorporated by reference herein in its entirety.

What is claimed is:

1. A medical image processing apparatus comprising:
an image information processor that generates image information for acquiring a superposed image having a three-dimensional image of a medical device over a three-dimensional image of a preoperative structure of an object to which the medical device is inserted, and outputs the image information on the superposed image,
wherein the image information processor generates a three-dimensional image of the preoperative structure by segmenting a plurality of preoperative two-dimensional tomograms, further wherein each of the two-dimensional tomograms has a marker as a coordinate reference, and
wherein the image information processor calculates a form and a position of the medical device from a curvature state of the medical device, a position where the medical device is mounted, and the marker and generates a three-dimensional image of the medical device in the superposed image.

2. The medical image processing apparatus according to claim 1, further comprising:
a curvature deformation detection unit that detects a deformation of the medical device, wherein the image information processor generates a change-of-form information on the medical device, wherein the change-of-form information is at least one information piece selected from change-of-angle information, change-of-tilt information, and change-of-pressure information detected by the curvature deformation detection unit.

3. The medical image processing apparatus according to claim 1, wherein each of the two-dimensional tomograms has a wider area image than an image corresponding to the image information on the superposed image output by the image information processor and displayed by a display apparatus.

4. The medical image processing apparatus according to claim 1, wherein the image information processor outputs the image information on the superposed image by transmitting the image information on the superposed image to a display apparatus by radio.

5. The medical image processing apparatus according to claim 2, wherein the image information processor determines that the curvature deformation unit is in contact with an internal structure of the object from the change-of-form information, and outputs an instruction to retract the inserted medical device from the object.

* * * * *